US009068928B2

(12) United States Patent
Kudenov

(10) Patent No.: US 9,068,928 B2
(45) Date of Patent: Jun. 30, 2015

(54) WHITE LIGHT SAGNAC INTERFEROMETER POLARIMETERS

(75) Inventor: Michael W. Kudenov, Tucson, AZ (US)

(73) Assignee: The Arizona Board of Regents on Behalf of the University of Arizona, Tucson, AZ (US)

(*) Notice: Subject to any disclaimer, the term of this patent is extended or adjusted under 35 U.S.C. 154(b) by 530 days.

(21) Appl. No.: 13/225,315

(22) Filed: Sep. 2, 2011

(65) Prior Publication Data

US 2012/0176622 A1 Jul. 12, 2012

Related U.S. Application Data

(60) Provisional application No. 61/402,767, filed on Sep. 3, 2010.

(51) Int. Cl.
*G01N 21/21* (2006.01)
*G01J 4/04* (2006.01)

(52) U.S. Cl.
CPC .. *G01N 21/21* (2013.01); *G01J 4/04* (2013.01)

(58) Field of Classification Search
USPC ................................. 356/451, 453, 456, 495
See application file for complete search history.

(56) References Cited

U.S. PATENT DOCUMENTS

| | | | |
|---|---|---|---|
| 5,781,293 A | 7/1998 | Padgett et al. | |
| 6,674,532 B2 | 1/2004 | VanDelden | |
| 6,687,007 B1 * | 2/2004 | Meigs | 356/456 |
| 2003/0142318 A1 | 7/2003 | Kuiseko | |
| 2005/0237532 A1 | 10/2005 | Beale et al. | |
| 2006/0250616 A1 * | 11/2006 | Pettipiece et al. | 356/456 |
| 2008/0278675 A1 | 11/2008 | Escuti et al. | |
| 2010/0110363 A1 | 5/2010 | Escuti et al. | |
| 2010/0171952 A1 | 7/2010 | DeFlores et al. | |
| 2010/0225856 A1 | 9/2010 | Escuti et al. | |

OTHER PUBLICATIONS

Oka and Saito, "Snapshot complete imaging polarimeter using Savart plates," Proc. SPIE 6295:629508 (2006).
Oka and Kaneko, "Compact complete imaging polarimeter using birefringent wedge prisms," Opt. Exp. 11:1510-1519 (2003).
Mujat et. al., "Interferometric imaging polarimeter," JOSA A:21:2244-2249 (2004).
Kudenov, et al., "White light Sagnac interferometer for snapshot linear polarimetric imaging," Opt. Exp. 17(25):22520-22534 (2009).
Kudenov, et al., "Prismatic imaging polarimeter calibration for the infrared spectral region," Opt. Exp. 16(18):13720-13737 (2008).

(Continued)

*Primary Examiner* — Hwa Lee
(74) *Attorney, Agent, or Firm* — Klarquist Sparkman, LLP

(57) ABSTRACT

Snapshot imaging polarimeters comprise Sagnac interferometers that include diffraction gratings situated to produce shear between counter-propagating optical fluxes produced by a polarizing beam splitter. The counter-propagating, sheared optical fluxes are focused onto a focal plane array to produce fringe patterns. The fringe patterns correspond to a scene polarization distribution modulated onto a spatial carrier frequency associated with a diffraction order. Multi-blazed gratings can be used so that modulations at a plurality of spatial frequencies are produced, with each spatial frequency corresponding to a spectral component of an input optical flux. Modulated fringe patterns can be demodulated to obtain scene Stokes parameter distributions.

19 Claims, 10 Drawing Sheets

(56) References Cited

OTHER PUBLICATIONS

Luo et al., "Compact and miniature snapshot imaging polarimeter," Applied Optics 47(24):4413-4417 (2008).
Courtial et al., "Design of a Static Fourier-Transform Spectrometer with Increased Field of View," *App. Op.* 35(34):6698-6702 (Dec. 1, 2006).
Crawford et al., "Liquid-crystal diffraction gratings using polarization holography alignment techniques," *J. Appl. Phys.* 98:123102 (2005).
Escuti et al., "Simplified Spectropolarimetry Using Reactive Mesogen Polarization Gratings," *Proc. SPIE* 6302:630207 (2006).
Hirai et al., "Application of Multiple-Image Fourier Transform Spectral Imaging to Measurement of Fast Phenomena," *Opt. Rev.* 1:205-207 (1994).
Kim et al., "Snapshot imaging spectropolarimeter utilizing polarization gratings," *Proc. of SPIE*, 7086:708603-1-708603-10 (2008).
Kudenov et al., "White-Light Channeled Imaging Polarimetry Using Broadband Polarization Gratings," *Appl. Opt.* 50:2283-2293 (2011).
Luo, "Snapshot Imaging Polarimeters Using Spatial Modulation," Ph.D. Dissertation, College of Optical Science, University of Arizona, (May 2008).
Oh and Escuti, "Achromatic Diffraction from Polarization Gratings with High Efficiency," *Opt. Lett.* 33:2287-2289 (2008).
Oh and Escuti, "Numerical Analysis of Polarization Gratings Using the Finite-Difference Time-Domain Method," *Phys. Rev. A* 76(4):043815 (2007).
Snik et al., "Spectral Modulation for Full Linear Polarimetry," *Appl. Opt.* 48(7):1337-1346 (2009).
The Art and Science of Amateur Experimentalism, Sciencemadness Discussion Board, http://www.sciencemadness.org/talk/viewthread.php?tid=13554, downloaded Apr. 15, 2012.
Tyo et al., "Review of Passive Imaging Polarimetry for Remote Sensing Applications," *Appl. Opt.* 45(22):5453-5469 (2006).
Walraven R., "Polarization Imagery," Optical Engineering, 20(1):014-018 (1981).
Wang et al., "Anisotropic Wet Etching on Birefringent Calcite Crystal," *Appl. Phys. A* 81:851-854 (2005).
Wyant, "OTF Measurements with a White Light Source: An Interferometric Technique," *App. Opt.* 14:1613-1615 (1975).

\* cited by examiner

WHITE LIGHT SAGNAC INTERFEROMETER POLARIMETERS

CROSS REFERENCE TO RELATED APPLICATION

This application claims the benefit of U.S. Provisional Application 61/402,767, filed on Sep. 3, 2010, which is incorporated herein by reference.

FIELD

The disclosure pertains to imaging polarimeters using a Sagnac interferometer configuration.

BACKGROUND

Polarization images can yield higher contrast than intensity images, providing the opportunity for dramatically improved object identification. Furthermore, incorporation of a polarimeter into a detection system allows for the potential to ascertain the Stokes parameter elements of a scene, thereby giving a complete identification of the polarization state of light reflected or emitted from objects in the scene. From such an analysis, the spatially varying two-dimensional state of polarization (SOP) can be determined.

SOP analysis is a useful technique for object characterization and distinction, particularly for differentiating man made versus natural objects. This is particularly valuable in the thermal infrared; if objects in a scene are emitting close to the background temperature of the environment (i.e., they are close to thermal equilibrium with their environment), then thermal detection typically yields ambiguous results. Addition of polarimetry data can often significantly enhance images of such objects as polarimetry can supply information that is unavailable by intensity imaging. For example, typical long-wavelength infrared (LWIR) intensity images provide little indication of the presence of a vehicle in the shadows of tree, while a polarization image makes the presence of an automobile obvious due to polarization associated with the smooth surfaces of the automobile.

Current techniques for imaging polarimetry include rotating retarder polarimeters. Through a series of sequential measurements, the complete spatial distribution of Stokes parameters in a scene can be determined. This method has several significant limitations. Rotating parts can lead to vibrational and mechanical problems. Images of dynamic scenes can also contain polarization artifacts as a result of combining a series of measurements. Other problems are related to oversampling and spatial synchronization.

Some of the problems with rotating retarder imaging polarimetry can be addressed with "snapshot" systems that do not require dynamic components, but instead take advantage of spatial carrier fringes and Fourier reconstruction techniques in order to provide a complete polarization analysis of a scene. Examples of such approaches are described in Oka and Saito, "Snapshot complete imaging polarimeter using Savart plates," Proc. SPIE 6295:629508 (2008) and Oka and Kaneko, "Compact complete imaging polarimeter using birefringent wedge prisms," Opt. Exp. 11:1510-1519 (2003), both of which are incorporated herein by reference. These approaches use birefringent materials to produce polarization dependent phase differences to produce snapshot images.

One example of such a snapshot system is based on a pair of Savart plates (SPs) introduced in a collimated space in an imaging system. An SP shears incident radiation using crystal birefringence to produce two laterally displaced, orthogonally polarized beams. By combining two orthogonal SPs, an incident optical flux is sheared to create four separate beams. After transmission by an analyzer, these beams are recombined with a lens, resulting in amplitude modulated interference fringes containing state of polarization (SOP) information on the image plane.

While such SP systems are impressive in their snapshot capabilities, they suffer from significant limitations. Due to the reliance on interference effects, the temporal coherence of imaging radiation presents a constraint in that the visibility of the interference fringes is inversely proportional to the spectral bandwidth. For instance, in the LWIR (8-12 μm wavelengths), a fringe visibility of 50% at a mean wavelength of 10 μm requires limiting optical bandwidth $\Delta\lambda_{50\%} \approx 373$ nm, which is a significant constraint with respect to the signal to noise ratio (SNR) of the acquired data. In addition, SP polarimeters require SPs which can be expensive due to the birefringent crystals required. In many wavelength regimes, especially the infrared, the required large crystals (clear apertures>25 mm with thicknesses>10 mm) are either unavailable or prohibitively expensive. Moreover, materials suitable for LWIR use such as CdSe or CdS have birefringences $B=|n_e-n_o|$ that are approximately 10 times less than those of materials suitable for use at visible wavelengths. As a result, thick crystals are needed.

These birefringent material limitations can be avoided through the implementation of a reflective interferometric scheme. Mujat et. al., "Interferometric imaging polarimeter," JOSA A:21:2244-2249 (2004), which is incorporated herein by reference, discloses an interferometric imaging polarimeter based on a modified Sagnac interferometer. In this system, a polarizing beam splitter is used to transmit an input beam into an interferometer, and a phase difference between orthogonal polarizations produced by displacing one of the mirrors in the interferometer is used to create an interference pattern. Irradiance measurements and coherence matrix techniques are then employed to determine the state of polarization from a set of two temporally spaced images. These methods are subject to similar registration problems that plague rotating retarder polarimeters for dynamic scenes.

SUMMARY

White light polarization Sagnac interferometers and associated methods are disclosed herein. In some examples, so-called "snapshot imaging polarimeters" are described that operate over broad wavelength ranges, including thermal infrared wavelengths and visible optical wavelengths. Diffraction gratings, in combination with reflective surfaces that define a Sagnac interferometer, produce a shear that is proportional to wavelength so that white-light broadband interference fringes are produced. In some examples, complete polarization data for a scene of interest is produced as all four Stokes parameters, while in other examples, only one or several polarization characteristics are determined such as one or more of the Stokes parameters. Stokes parameters are encoded onto a sequence of one or two dimensional spatial carrier frequencies so that a Fourier transformation of a generated fringe pattern enables reconstruction of the Stokes parameter distribution. Representative applications include white-light MTF measurements, as well as testing optical surfaces.

According to some examples, polarimeters comprise an interferometer configured to produce a dispersion compensated shear between first and second portions of an input light flux. A detector is situated to receive an output light flux corresponding to a combination of the sheared first and second portions of the input light flux and produce an image signal, and an image processor is configured to produce a polarization image based on the image signal. In representative examples, the interferometer is a Sagnac interferometer that includes a pair of diffraction gratings. In further examples, the interferometer includes a polarizing beam splitter and at least two mirrors situated so that the first portion and the second portion of the input light are reflected and transmitted, respectively, by the polarizing beam splitter, the at least two mirrors and the polarizing beam splitter defining an interferometer optical path. At least two diffraction gratings are situated along the interferometer optical path so as to diffract the first portion and the second portion of the input optical flux to produce the dispersion compensated shear.

In some embodiments, the at least two mirrors comprise a first mirror and a second mirror, and the at least two diffraction grating comprises a first diffraction grating and a second diffraction grating, the first diffraction grating and the second diffraction grating situated along the interferometer optical path between the first mirror and the polarizing beam splitter and the second mirror and the polarizing beam splitter, respectively. In typical examples, the first and second gratings are configured so that diffraction of the first and second portions of the input optical flux by both of the first and second gratings directs the first and second beams so as to be directed along the interferometer optical path and to propagate displaced from and parallel to the interferometer optical axis at the polarizing beam splitter. In some examples, the first and second diffraction gratings are situated a distance b from the first mirror and the second mirror respectively, and the first mirror and the second mirror are separated by a distance a along the interferometer optical path such that the shear is proportional to $(a+2b)\lambda$, wherein $\lambda$ is a wavelength associated with the input optical flux.

According to additional examples, the first and second gratings have a common grating period and are situated with respect to the interferometer axis so as diffract into a common diffraction order m and produce shear that is proportional to the grating diffraction order m. In some embodiments, the image processor is configured to select at least one spatial frequency component of the recorded image signal and determine an image polarization characteristic based an intensity modulation associated with an image signal variation at the selected spatial frequency.

In other representative examples, shear for a spectral component of the input optical flux is proportional to a wavelength associated with the spectral component, and the polarization image is a two dimensional image. According to some examples, the shear is associated with spatial frequency components for a plurality of input optical flux spectral components, and the image processor is configured to estimate at least one polarization characteristic associated with the spatial frequency components based on image signal modulation at the corresponding spatial frequency. In other examples, the interferometer is configured to produce shear between first and second portions based on counter-propagation of the first and second portions of the input light flux.

Methods comprising receiving an input optical flux and producing a shear between first and second portions of the input optical flux that is proportional to a wavelength of the input optical flux by directing the first and second portions along optical paths in an interferometer. A polarization characteristic of the input optical flux is estimated based on a spatial frequency in an intensity pattern obtained by combining the sheared first and second portions of the input optical flux. In some embodiments, each of the first and second portions of the incident optical flux are diffracted at least one diffraction grating so as to produce a shear having a magnitude associated with a grating period and diffraction order. In some examples, the shear is inversely proportional to a grating period and directly proportional to a grating order. In additional examples, the first and second portions are combined with at least one focusing optical element of focal length f, wherein the spatial frequency is inversely proportional to f. In representative embodiments, the first and second portions of the input optical flux are directed along counter-propagating optical paths in a Sagnac interferometer. In further examples, spatial frequencies are selected for at least two optical spectral components, and the first and second portions of the input optical flux are directed to at least two diffraction gratings that are situated to diffract the at least two optical spectral components into different diffraction orders. In additional examples, the interferometer includes a polarizing beam splitter and a first and a second diffraction grating situated to receive components of the input optical flux from a polarizing beam splitter such that the first and second gratings direct the received components to respective reflective surfaces so that the spatial frequency is a function of the separations between the diffraction gratings and the associated reflective surfaces, and a separation of the reflective surfaces.

Polarimeters comprise a Sagnac interferometer defined by a polarizing beam splitter, first and second diffraction gratings and associated first and second reflectors, such that first and second polarization components of an optical flux directed to the polarization beam splitter counter-propagate from the polarizing beam splitter, the first polarization component propagating to the first grating, the first reflective surface, the second reflective surface, the second grating, and the polarization beam splitter and the second polarization component propagating to the second grating, the second mirror, the first grating and to the polarization beam splitter. A focusing element is situated to combine the counter-propagating portions of the input optical flux to produce an intensity pattern, and a detector is configured to receive the intensity pattern and produce a detected intensity pattern. An image processor is configured to produce a polarization image based on the detected intensity pattern. In typical examples, the Sagnac interferometer produces a shear between first and second counter-propagating polarization components, wherein the shear is a function of at least one of a diffraction grating period, a diffraction order, a separation of diffraction gratings and respective reflective surfaces, and a separation of the first and second reflective surface.

The foregoing and other features, and advantages of the disclosed technology will become more apparent from the following detailed description, which proceeds with reference to the accompanying figures.

DETAILED DESCRIPTION

Figure 1A:
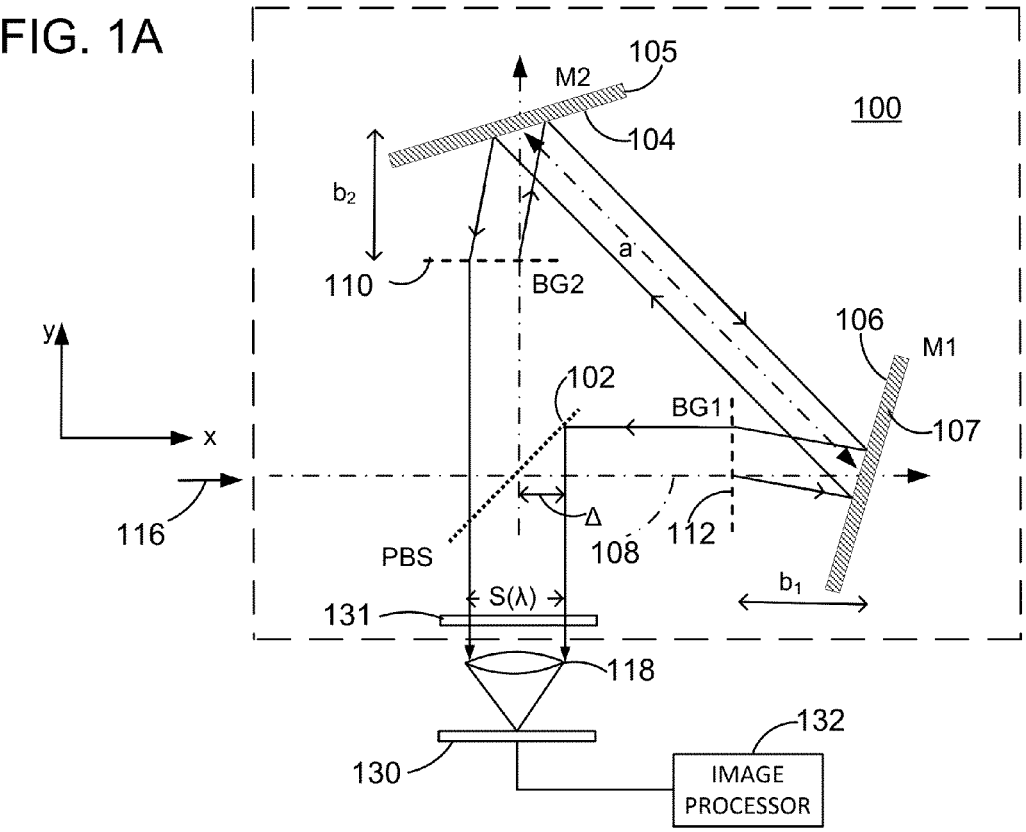
FIG. 1A illustrates a modified Sagnac interferometer configured to produce shear between counter-propagating optical fluxes using two diffraction gratings.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

As used herein, an optical flux refers to electromagnetic radiation in a wavelength range of from about 100 nm to about 100 μm. In some examples, an optical flux has a spectral width that can be as large as 0.5, 1, 2, 5, or 10 times a center wavelength, or can comprises a plurality of spectral components extending over similar spectral bandwidths. Such optical fluxes can be referred to as large bandwidth optical fluxes. Typically, an optical flux is received from a scene of interest and amplitude, phase, spectral, or polarization modulation (or one or more combinations thereof) in the received optical flux is processed based on a detected image associated with a spatial variation of the optical flux which can be stored in one or more computer-readable media as an image file in a JPEG or other format. In the disclosed examples, so-called "snapshot" imaging systems are described in which image data associated with a plurality of regions or locations in a scene of interest (typically an entire two dimensional image) can be obtained in a single acquisition of a received optical flux using a two dimensional detector array. However, images can also be obtained using one dimensional arrays or one or more individual detectors and suitable scanning systems. In some examples, an image associated with the detected optical flux is stored for processing based on computer executable instruction stored in a computer readable medium and configured for execution on general purpose or special purpose processor, or dedicated processing hardware. In addition to snapshot imaging, sequential measurements can also be used. For convenience, examples that provide two dimensional images are described, but in other examples, one dimensional (line) images or single point images can be obtained.

For convenience, optical systems are described with respect to an axis along which optical fluxes propagate and along which optical components are situated. Such an axis is shown as bent or folded by reflective optical elements. In the disclosed embodiments, an xyz-coordinate system is used in which a direction of propagation is along a z-axis (which may vary due to folding of the axis) and x- and y-axes define transverse planes. Typically the y-axis is perpendicular to the plane of the drawings and the x-axis is perpendicular to the y-axis and the z-axis and is in the plane of the drawings.

In representative examples, the imaging polarimetry methods and apparatus disclosed herein can be used to estimate a 2-dimensional spatial Stokes parameter distribution of a scene in order to characterize aerosol size distributions, distinguish manmade targets from background clutter, evaluate distributions of stress birefringence in quality control, evaluate biological tissues in medical imaging, or for other purposes. While in typical examples, image data is evaluated so as to correspond to one or more components of a Stokes vector, data can be processed to obtain other polarization characteristics such as ellipticity or can be based on other representations such as those associated with Jones matrices.

In the disclosed embodiments, interferometers are configured to include diffraction gratings so as to produce a shear between orthogonally polarized components of an input optical flux that is proportional to a wavelength of the input optical flux. For large bandwidth optical fluxes, shear for each spectral component is proportional to a wavelength of the spectral component. A shear between optical fluxes that varies linearly with flux wavelength is referred to herein as a dispersion-compensated shear. In some examples, polarimeters include optical systems that can provide a total shear that includes a dispersion compensated shear and a dispersive shear. As discussed below, a dispersion compensated shear is associated with interference patterns having amplitude modulations at a spatial frequency that is independent of optical wavelength.

Polarization properties of a scene can be conveniently described using a Stokes vector. A scene Stokes vector S(x,y), is defined as:

$$S(x, y) = \begin{bmatrix} S_0(x, y) \\ S_1(x, y) \\ S_2(x, y) \\ S_3(x, y) \end{bmatrix} = \begin{bmatrix} I_0(x, y) + I_{90}(x, y) \\ I_0(x, y) - I_{90}(x, y) \\ I_{45}(x, y) - I_{135}(x, y) \\ I_R(x, y) - I_L(x, y) \end{bmatrix}, \quad (1)$$

wherein x, y are spatial coordinates in the scene, $S_0$ is the total power of the beam, $S_1$ denotes a preference for linear polarization at 0° over linear polarization at 90°, $S_2$ denotes a preference for linear polarization at 45° over linear polarization at 135°, $S_3$ denotes a preference for right circular over left circular polarization states, and I(x,y) refers to optical flux intensity. By measuring all four elements of S(x,y), a complete spatial distribution of the polarization state associated with an scene can be determined. The Stokes vector permits assessment of partially polarized optical fluxes and determination of an extent of polarization as, for example, $$\frac{(S_1^2 + S_2^2 + S_3^2)^{1/2}}{S_0}.$$

As discussed above, some conventional approaches to measuring scene Stokes parameters are based on recording multiple intensity measurements sequentially using different configurations of polarization analyzers. The Stokes parameters can then be calculated using Mueller matrices. However, time-sequential measurements of a rapidly changing scene are susceptible to temporal misregistration. The disclosed methods and apparatus can reduce or eliminate such misregistration errors by acquiring scene image data in a single snapshot. Sequential measurements can be made as well, if desired.

According to representative examples, interferometrically generated carrier frequencies are amplitude modulated with spatially-dependent 2-dimensional Stokes parameters associated with a scene to be imaged. Such methods can be referred to as channeled image polarimetry (CIP) methods. In typical examples, all the Stokes parameters are directly modulated onto coincident interference fringes so that misregistration problems are eliminated, and images can be acquired with readily available lenses and cameras.

Example 1

Symmetric Grating Based Embodiments

For convenient illustration, representative embodiments are described in which diffraction gratings are symmetrically situated in a Sagnac interferometer with respect to reflectors that define counter-propagating optical paths. Following this description, other examples with arbitrary grating placements are described.

With reference to FIG. 1A, a representative Sagnac interferometer 100 includes a polarizing beam splitter (PBS) 102, and reflective surfaces 104, 106 that define an interferometer optical path 108. For convenience, the path 108 is also referred to as an interferometer axis herein. As shown in FIG. 1A, the interferometer axis 108 is folded by the reflective surfaces 104, 106. Blazed transmission gratings (BGs) 110, 112, are situated along the axis 108 at an axial distances $b_1, b_2$ from the reflective surfaces 106, 104, respectively. The PBS 102 is configured to receive an input optical flux 116 that is directed along the axis 108 so that portions of the input optical flux 116 are reflected or transmitted to respective reflective surfaces 104, 106 and the associated BGs 110, 112. As shown in FIG. 1A, the reflected and transmitted portions of the input optical flux counter-propagate in the interferometer 100. Typically, the input flux 116 is a collimated optical flux associated with an image scene, and a lens 118 is situated to receive and combine the counter-propagating portions of the input optical flux received from the PBS 102 after transmission by a polarization analyzer 131.

The PBS 102 can be a thin-film based beam splitter such as a polarizing beam splitter cube, a wire grid beam splitter (WGBS), or other polarization dependent beam splitter. The blazed diffraction gratings can be ruled gratings, holographic gratings, or other types of gratings. Reflective surfaces such as the surfaces 104, 106 can be provided as metallic coatings, polished metal surfaces, dielectric coatings, or based on total internal reflection. As shown in FIG. 1A, the reflective surfaces 104, 106 are provided by respective mirrors 105, 107.

The input optical flux 116 is divided into orthogonal polarization components by the polarizing beam splitter 102 and the components are directed along respective arms of the interferometer 100. For example, the portion of the light flux 116 transmitted by the PBS 102 is directed along the axis 108 to the diffraction grating 112 to the reflective surface 106. As shown in FIG. 1A, the reflective surface 106 is situated a distance $b_1$ from the BG 112 measured along the axis 108. The diffraction grating 112 diffracts at least a portion of the incident flux into a single diffraction order at an angle θ, given by a diffraction equation as θ≈mλ/d for small angles, wherein m is an order of diffraction and d is the period of the grating. The resulting diffracted optical flux is then reflected by the reflective surface 106 to the reflective surface 104 and then to the diffraction grating 110 so as to be incident to the diffraction grating 110 at the angle θ and is thereby diffracted so as to propagate parallel to but displaced a distance Δ from the axis 108. The displaced flux is then directed by the PBS 102 to the lens 118. The counter-propagating optical flux (i.e., the flux reflected by the PBS 102) is similarly displaced a distance Δ from the axis 108, but in an opposite direction and is directed to the lens 118 so that the counter-propagating fluxes are combined at a focal plane array detector 130 or other detector. A detected intensity distribution can be stored in one or more computer readable media for processing by an image processor 132.

Figure 10:
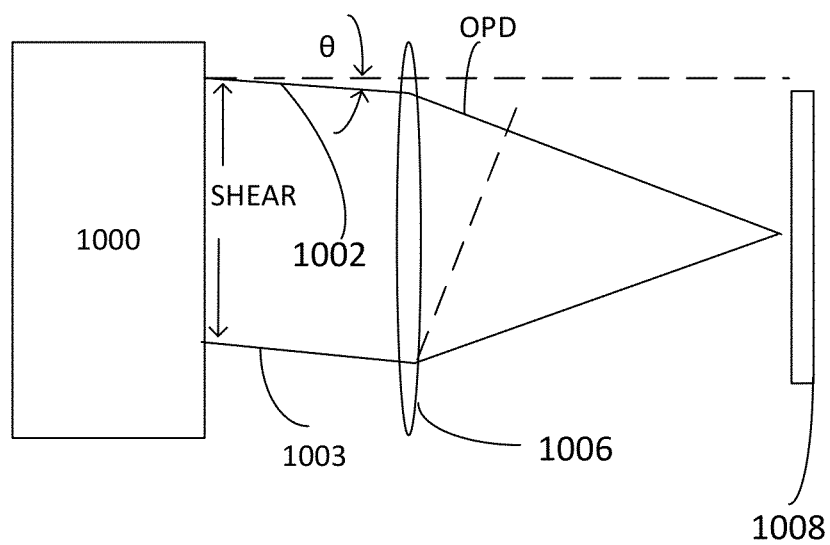
FIG. 10 illustrates determination of an optical path difference (OPD) associated with shear.

Optical path difference (OPD) associated with a focused, sheared optical flux is illustrated in FIG. 10. As shown in FIG. 10, a shearing optical system 1000 such as described above produces shear $S_{shear}$ between flux portions propagating along ray directions 1002, 1003 to a lens 1006 that combines the flux portions at a focal plane array (FPA) 1008 or other detector. For convenient illustration, the lens 1006 is shown as a singlet lens, but in other examples, multi-element lenses, reflective optics, or catadioptric optics can be used. Referring to FIG. 10, $$OPD = S_{shear} \sin(\theta) \approx S_{shear} \theta,$$

for small angle θ. In FIG. 10, θ is depicted as an angle in the object space of the lens 1006 with respect to ray directions 1002, 1003. This assumes that the singlet lens 1006 has an aperture stop that is located at the lens 1006. In this special case, θ is the angle of the chief ray in both object and image space. However, in more sophisticated lens systems, θ is the angle of the chief ray in image space.

When the two sheared portions of the optical flux are combined by the lens, interference fringes are produced on the FPA 1008. This interference can be expressed as $$I(x_i, y_i) = \left\langle \left| \frac{1}{\sqrt{2}} E_x(x_i, y_i, t)e^{-j\phi_1} + \frac{1}{\sqrt{2}} E_y(x_i, y_i, t)e^{-j\phi_2} \right|^2 \right\rangle,$$

where $\langle \rangle$ represents a time average, $x_i$ and $y_i$ are image-plane coordinates, and $\phi_1$, $\phi_2$, are the cumulative phases along each ray. Expansion of this expression yields $$I(x_i, y_i) = \frac{1}{2} \left\{ \begin{array}{c} (\langle E_x E_x^*\rangle + \langle E_y E_y^*\rangle) + (\langle E_x E_y^*\rangle + \langle E_x^* E_y\rangle)\cos(\phi_1 - \phi_2) + \\ j(-\langle E_x E_y^*\rangle + \langle E_x^* E_y\rangle)\sin(\phi_1 - \phi_2) \end{array} \right\},$$

where $E_x$, $E_y$ are now understood to be functions of image plane coordinates $x_i$ and $y_i$. The phase factors are $$\phi_1 = \frac{2\pi\Delta}{\lambda f_{obj}} x_i \text{ and } \phi_2 = -\frac{2\pi\Delta}{\lambda f_{obj}} x_i.$$

The Stokes parameters are defined from the components of the electric field as $$\begin{bmatrix} S_0 \\ S_1 \\ S_2 \\ S_3 \end{bmatrix} = \begin{bmatrix} \langle E_x E_x^*\rangle + \langle E_y E_y^*\rangle \\ \langle E_x E_x^*\rangle - \langle E_y E_y^*\rangle \\ \langle E_x E_y^*\rangle + \langle E_x^* E_y\rangle \\ j(\langle E_x E_y^*\rangle - \langle E_x^* E_y\rangle) \end{bmatrix}.$$

Re-expressing I using the definitions of the Stokes parameter and $\phi_1$, $\phi_2$, yields $$I(x_i, y_i) = \frac{1}{2}\left[ S_0 + S_2 \cos\left(\frac{4\pi\Delta}{f_{obj}}x_i\right) - S_3 \sin\left(\frac{4\pi\Delta}{f_{obj}}x_i\right) \right]$$

Consequently, the shear modulates $S_2$ and $S_3$ onto a carrier frequency, while $S_0$ remains as an un-modulated component. The carrier frequency U is a function of shear and is given by $$U = \frac{2\pi S(\lambda)}{\lambda f} \tag{2}$$

Fourier filtering can then be used to calibrate and reconstruct the spatially-dependent Stokes parameters over the image plane.

Figure 1B:
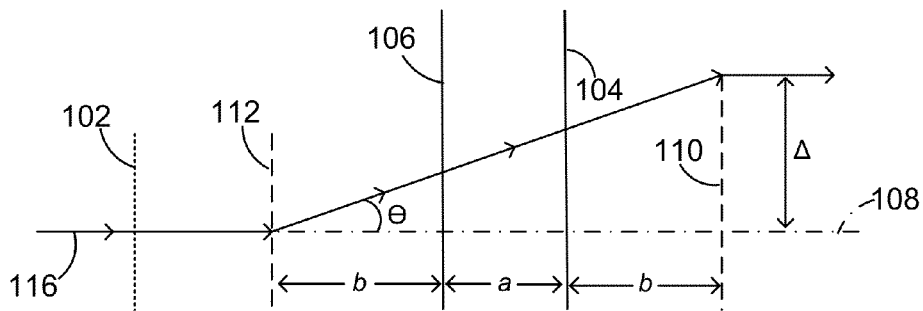
FIG. 1B is an unfolded view of a portion of the interferometer of FIG. 1A.

The determination of the displacement $\Delta$ as a function of interferometer geometry is illustrated in the partial unfolded layout of FIG. 1B. The displacement $\Delta$ is dependent on the grating-reflective surface axial separations $b_1=b_2=b$ and the axial separation a of the reflective surfaces 104, 106. For small angles, the angular deviation $\theta$ from the on-axis path can be expressed as:

$$\theta \approx \frac{m\lambda}{d} \approx \frac{\Delta}{2b+a}, \tag{3}$$

wherein $\lambda$ is the optical flux and m is a diffraction order. The total shear S $(\lambda)=2\Delta$ can then be expressed as:

$$S(\lambda) = 2\Delta = \frac{m\lambda}{d}(4b + 2a) \tag{4}$$

Thus, the generated shear is directly proportional to wavelength.

The focusing lens 118 combines the sheared optical fluxes at the detector 130 so as to produce fringes (i.e., intensity modulation) at a spatial carrier frequency U based on the total shear, i.e., at a spatial carrier frequency U given by:

$$U = \frac{2\pi S(\lambda)}{\lambda f} = \frac{2\pi m(4b + 2a)}{df}, \tag{5}$$

wherein f is a focal length of the lens 118, and d is a grating period.

In some examples, gratings of different periods and situated to diffract at different orders are used, and the shear is given by:

$$S(\lambda) = 2\Delta = \lambda\left(\frac{m_1}{d_1} + \frac{m_2}{d_2}\right)(2b + a),$$

wherein $m_1$ and $m_2$ are grating diffraction orders, and $d_1$ and $d_2$ are grating periods.

Because the shear is wavelength dependent, the spatial frequency U of the interference fringes which contain the polarization information from the scene is consequently wavelength independent in a paraxial approximation. As a result, high visibility fringes can be obtained for broadband optical sources, regardless of the spatial or temporal coherence of the received optical flux. In addition, a fringe period U can be selected by changing one or more of the reflective surface spacing a, grating spacings $b_1$, $b_2$, grating period d, diffraction order m, and focal length f of the lens 118. In the example of FIG. 1B, the grating-reflective surface spacing is the same for both the gratings 110, 112, but in other examples can be different.

The example of FIGS. 1A-1B is based on a Sagnac interferometer design in which the two optical fluxes to be combined counter-propagate along a common optical path. Thus, such a configuration tends to be resistant to vibration, and input optical fluxes of limited spatial and/or temporal coherence can be used. In other examples, gratings can be situated in interferometers of other configurations, particularly division of amplitude interferometers so as to produce similar shear. For example, diffraction gratings can be used in conjunction with a Mach-Zehnder interferometer to produce shear, although adequate interference fringe visibility may require appreciable optical flux coherence as the Mach Zehnder interferometer does not provide a common optical path. Accordingly, in applications to broad wavelength ranges, common path interferometers generally provide superior results.

In some applications, measurement of all four Stokes parameters is unnecessary. For example, $S_3$ is typically negligible in the thermal infrared and loss of the capability of measuring circular polarization (i.e., $S_3$) is of little consequence. If measurement of $S_3$ is unnecessary, an interferometer system similar to that of FIG. 1A can be provided with an achromatic quarter wave retarder situated with its fast axis at 45 degrees to the axis of the PBS 102 at an interferometer input. Such a configuration permits measurement of $S_0$, $S_1$, and $S_2$. An intensity distribution I(x, y) generated at a focal plane array with such a system can be expressed as:

$$I(x,y) = \tfrac{1}{2}S_0(x,y) - \tfrac{1}{2}|S_{12}(x,y)|\cos[2\pi Uy - \arg\{S_{12}(x,y)\}] \quad (6)$$

wherein U is the shear generated by the interferometer, $S_{12}=S_1+jS_2$, so that $|S_{12}|$ is a degree of linear polarization and arg $\{S_{12}\}$ is an orientation of the linear polarization.

Figure 2:
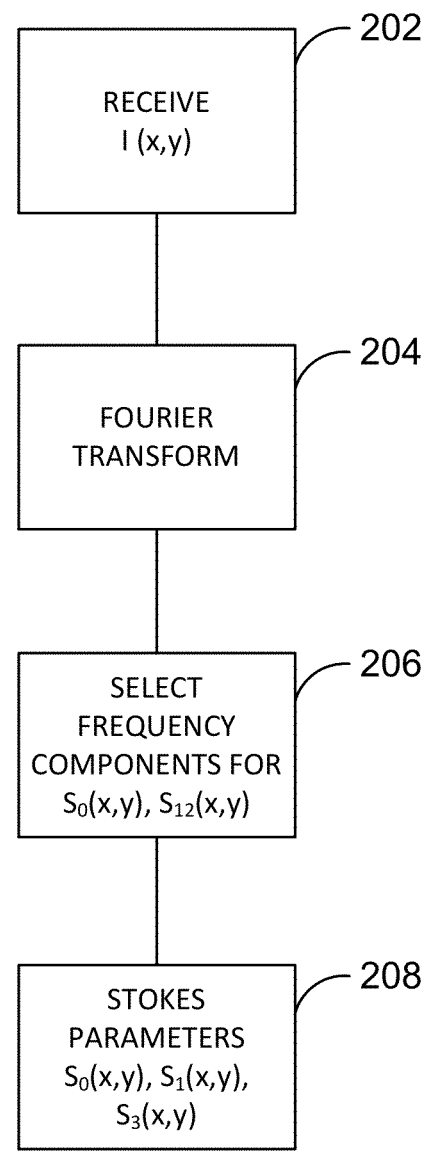
FIG. 2 illustrates an interferometer-based polarimeter configured that includes an input quarter wave retarder and configured for estimation of spatial distributions of Stokes parameters $S_0$, $S_1$, and $S_2$.

Stokes parameters can be extracted from this intensity distribution as shown in FIG. 2. A recorded fringe intensity I(x,y) is received at 202, and at 204, the recorded intensity is Fourier transformed with respect to the shear axis (in the example of FIGS. 1A-1B, a y-axis). At 206, spatial frequency components at zero frequency and at spatial frequency U are identified that are associated with particular combinations of Stokes parameters, such as $S_0(x,y)$ and $S_{12}=S_1+jS_2$ as shown above. At 208, spatial distributions of the Stokes parameters are calculated based on the selected frequency component. Typically, the selected components are inverse Fourier transformed for use in estimating the associated Stokes parameter distributions.

Figure 3:
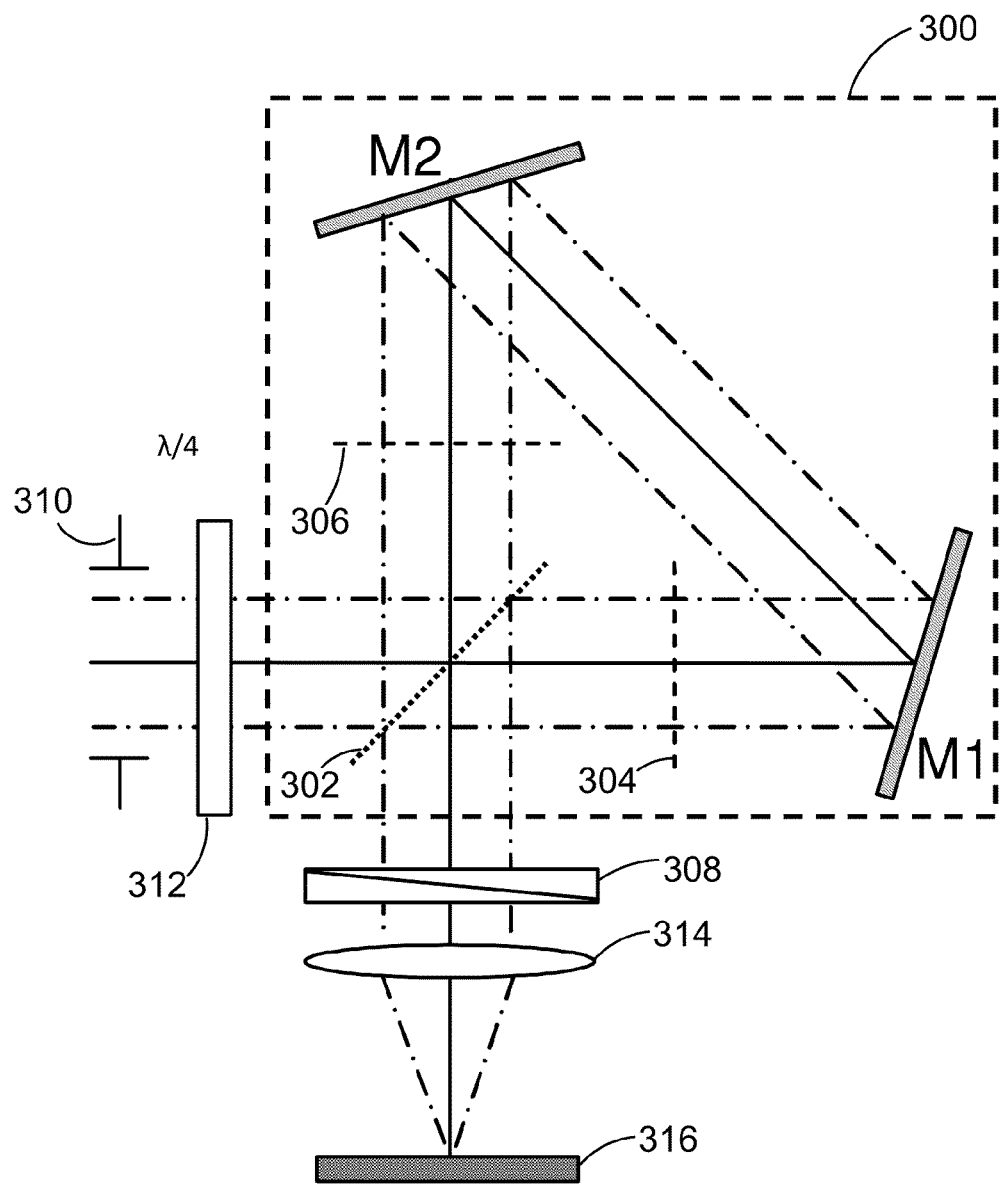
FIG. 3 illustrates an interferometer-based polarimeter that includes an input quarter wave retarder and output linear analyzer configured for estimation of spatial distributions of linear polarization.

A representative interferometer based polarimetry system configured to obtain a linear state of polarization distribution associated with a scene is illustrated in FIG. 3. As shown in FIG. 3, a modified Sagnac interferometer 300 includes an input PBS 302, diffraction gratings 304, 306 and an output linear polarizer 308. An optical flux associated with a scene is directed through an entrance aperture 310 and a quarter wave retarder 312 to the interferometer 300. An objective lens 314 is situated to produce an image that contains modulated polarization information on a focal plane array 316 by combining sheared, counter-propagating optical fluxes.

Example 2

Generalized Dispersion Compensated Sagnac Interferometer Systems

Figure 4A:
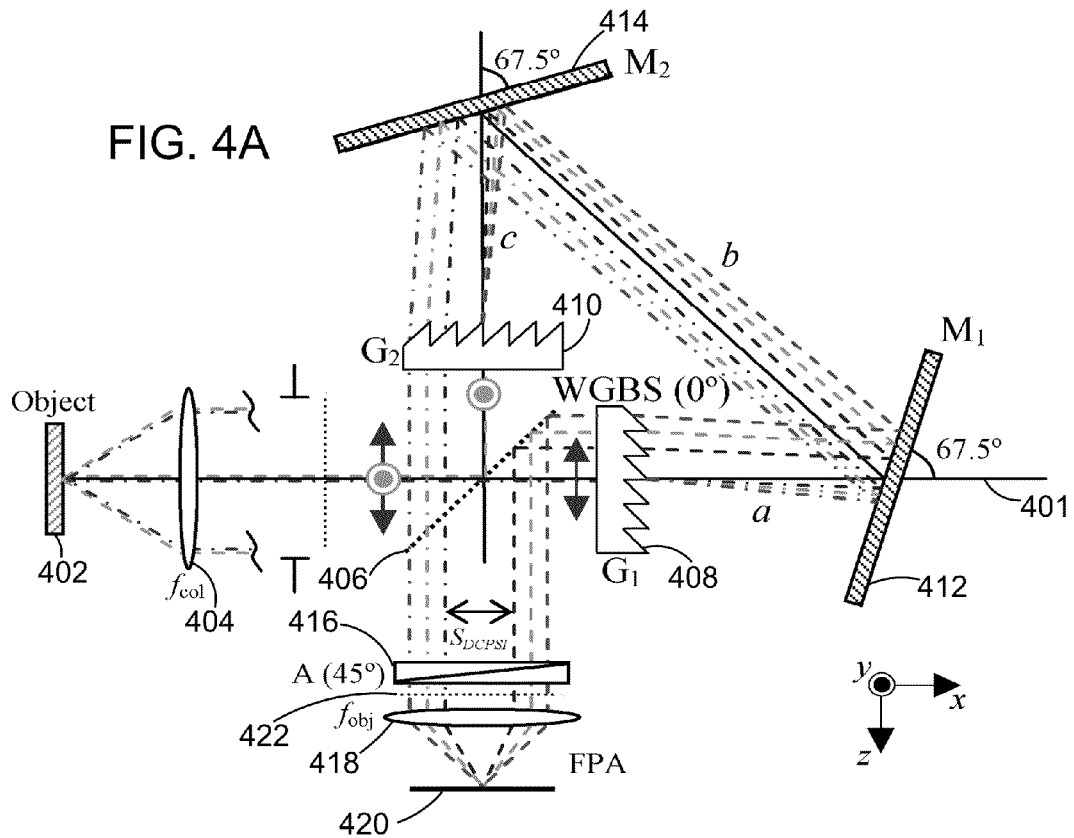
FIGS. 4A-4B illustrate propagation of multiple spectral components in a dispersion compensated interferometer that includes two blazed gratings.
Figure 4B:
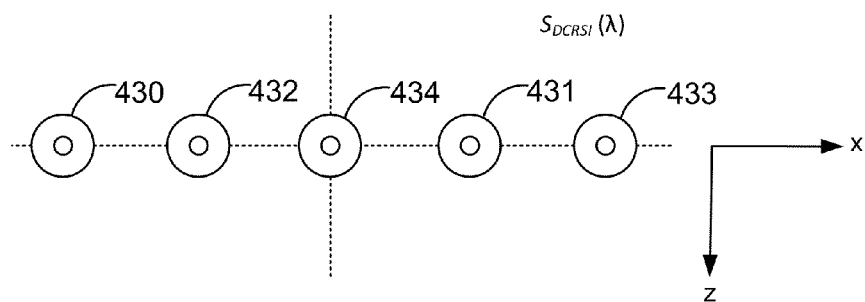

A generalized Sagnac interferometer based polarimeter is illustrated in FIGS. 4A-4B. As shown in FIG. 4A, an object 402 is situated on an axis 401 so that an optical flux from the object 402 is directed to a collimating lens 404 and to a PBS 406. In some examples, the collimating lens 404 can be omitted. A portion of the optical flux in a first polarization state (shown as in the plane of FIG. 4A) is directed through a first grating 408 to mirrors 412, 414, and then to a second grating 410 and the PBS 406. This portion is then directed to an analyzer 416 and focused by an objective lens 418 to a focal plane array 420. A portion of the input optical flux in a second polarization state (shown in FIG. 4A as perpendicular to the plane of FIG. 4A) is oppositely directed and is combined with the counter-propagating flux in the first polarization state at the focal plane array 420 by the lens 418. The combination of the counter-propagating fluxes at the focal plane array produces an interference pattern I(x,y) that can be used to determine one or more of the Stokes parameters or provide other indication of polarization.

For identical diffraction gratings $G_1$ and $G_2$ with grating period d, the shear $S_{DCPSI}$ is given by:

$$S_{DCPSI} = \frac{2m\lambda}{d}(a+b+c) \quad (7)$$

wherein a, b, and c represent the distances between $G_1$ and $M_1$, $M_1$ and $M_2$, and $M_3$ and $G_2$, respectively, and m is a diffraction order. FIG. 4B illustrates the sheared optical flux in a plane 422 that is perpendicular to a z-axis. An undiffracted component of the input flux is situated on axis at 434 while counter-propagating diffracted components associated with a longer and a shorter wavelength are displaced to locations 430, 433 and 432, 431, respectively.

The combined output optical flux as focused by the objective lens (focal length $f_{obj}$) produces an intensity distribution:

$$I_{DCPSI}(x_i, y_i) = \quad (8)$$

$$\frac{1}{2}\sum_{m=0}^{d/\lambda_{min}} S_0'(m) + \frac{1}{2}\sum_{m=1}^{d/\lambda_{min}} \left[ \begin{array}{l} S_2'(m)\cos\left(\dfrac{2\pi}{f_{obj}}\dfrac{2m}{d}(a+b+c)x_i\right) - \\ S_3'(m)\sin\left(\dfrac{2\pi}{f_{obj}}\dfrac{2m}{d}(a+b+c)x_i\right) \end{array} \right].$$

The intensity distribution $I_{DCPSI}$ is a summation from a diffraction order m=0 to a maximum diffraction order m=(d/$\lambda_{min}$)sin($\pi$/2), wherein $\lambda_{min}$ is a shortest wavelength component of a combined optical flux at the detector. The Stokes parameters $S_0'(m)$, $S_2'(M)$, and $S_3'(M)$ as weighted by grating diffraction efficiency $E(\lambda,m)$ are given by:

$$S_0'(m) = \int_{\lambda_{min}}^{\lambda_{max}} DE^2(\lambda, m) S_0(\lambda) \, d\lambda, \quad (9)$$

$$S_2'(m) = \int_{\lambda_{min}}^{\lambda_{max}} DE^2(\lambda, m) S_2(\lambda) \, d\lambda, \quad (10)$$

$$S_3'(m) = \int_{\lambda_{min}}^{\lambda_{max}} DE^2(\lambda, m) S_3(\lambda) \, d\lambda, \quad (11)$$

wherein $\lambda_{min}$ and $\lambda_{max}$ are the minimum and maximum wavelengths in the combined optical flux. Spatial carrier frequencies are given by:

$$U_{DCPSI} = \frac{2m}{df_{obj}}(a+b+c), \quad (12)$$

which is independent of wavelength (i.e., lacks dispersion), permitting white-light interference fringes to be generated. In addition, carrier frequency depends on the diffraction order m, and this dependence can be used in multispectral imaging by, for example, substituting multiple-order gratings for single order gratings. The diffraction efficiency weighted Stokes parameters can be obtained by demodulating $I_{DCPSI}$ with respect to one or more of spatial frequencies $U_{DCPSI}$.

Example 3

White Light Polarimetric Reconstructions in $S_1$ and $S_2$

A quarter wave retarder (QWR) oriented at 45° in front of a simplified channeled spectropolarimeter such as shown in FIG. 4A can be used to measure linear polarization ($S_0$, $S_1$, and $S_2$). The Mueller matrix for a QWR at 45° is $$M_{QWR,45°} = \begin{bmatrix} 1 & 0 & 0 & 0 \\ 0 & 0 & 0 & -1 \\ 0 & 0 & 1 & 0 \\ 0 & 1 & 0 & 0 \end{bmatrix}$$

Multiplication of this matrix by an arbitrary incident Stokes vector yields $$S_{out} = M_{QWR,45°}[S_0\,S_1\,S_2\,S_3]^T = [S_0\,-S_3\,S_2\,S_1]^T.$$

Therefore, the QWR converts any incident linear horizontal or vertical polarization states ($S_1$) into circular polarization ($S_3$) and vice versa. Consequently, with an included QWR, the detected intensity pattern becomes $$I_{DCPSI}(x_i, y_i) = \frac{1}{2}\sum_{m=0}^{d/\lambda_1} S'_0(m) + \frac{1}{2}\sum_{m=1}^{d/\lambda_1} \left[ \begin{array}{c} S'_2(m)\cos\left(\frac{2\pi}{f_{obj}}\frac{2m}{d}(a+b+c)x_i\right) - \\ S'_1(m)\sin\left(\frac{2\pi}{f_{obj}}\frac{2m}{d}(a+b+c)x_i\right) \end{array} \right],$$

wherein $S_1'(m)$ is analogous to $S_3'(m)$, and is defined as $$S'_1(m) = \int_{\lambda_1}^{\lambda_2} DE^2(\lambda, m)S_1(\lambda)\,d\lambda.$$

Inverse Fourier transformation of channels $C_0$ (zero frequency component) and $C_1$ (component at frequency $U_{DCPSI}$) yields $$\mathfrak{F}^{-1}[C_0] = \frac{S'_0(1)}{2}$$

$$\mathfrak{F}^{-1}[C_1] = \frac{1}{4}(S'_2(1) + jS'_1(1))\exp(j2\pi U_{DCPSI}x_i),$$

assuming that the m=1 diffraction order is dominant. Thus, a full linear polarization measurement including the degree of linear polarization (DOLP) and its orientation can be calculated from a single interference pattern. The DOLP and its orientation can be determined as:

$$DOLP = \frac{\sqrt{S_1^2 + S_2^2}}{S_0}$$

$$\phi = \frac{1}{2}\text{atan}\left(\frac{S_2}{S_1}\right).$$

Example 4

Dual-Band Snapshot Imaging Polarimeter

Figure 5:
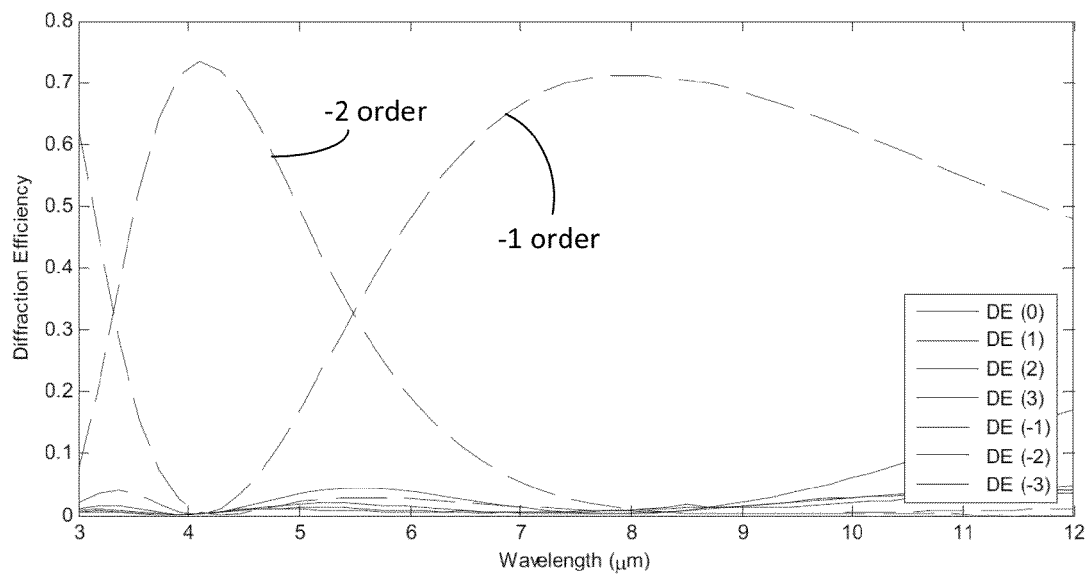
FIG. 5 is a graph of theoretical diffraction efficiency for a blazed grating designed for a wavelength of roughly 8 μm on a ZnSe substrate. Diffraction efficiencies for the 0, +/−1, +/−2, and +/−3 orders are shown.

Blazed gratings can have high diffraction efficiency into a single diffraction order at a design wavelength. At other wavelengths, a blazed grating can produce substantial diffraction into a plurality of diffraction orders. In some examples, polarization analysis can be provided in two or more wavelength bands that are nearly integer multiples of each other. For example, analysis in a combination of a midwavelength infrared band (MWIR) of about 3-5 µm and a long wavelength infrared band (LWIR) of about 8-12 µm can be provided. These wavelength bands are close to an integer separation in optical path difference so that a blazed grating designed for a +1 order at a wavelength of 8 µm will have maximum efficiency at 8 µm in the +1 order, 4 µm in the +2 order, 2 µm in the +3 order, etc. Therefore, a grating can be chosen to be suitable for both MWIR and LWIR bands. Diffraction efficiencies for a representative grating having a design wavelength of 8 µm at various diffraction orders is shown in FIG. 5. As shear is proportional to diffraction order, such a configuration produces twice as much shear in the MWIR than in the LWIR so that fringe spatial frequency in the MWIR is twice that in the LWIR. MWIR and LWIR image contributions can be separated by demodulation of the fringes based on corresponding fringe spatial frequencies. Other diffraction orders can also appear in the detected fringes, and these can be reduced or removed based on their differing spatial frequencies.

Example 5

Deep Grating Multispectral Snapshot Imaging Spectrometer

Figure 6:
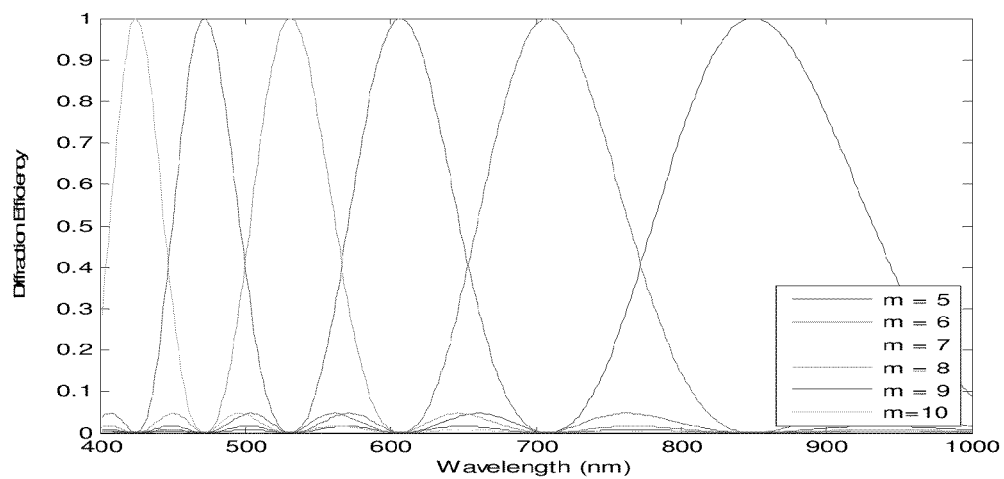
FIG. 6 is a graph of diffraction efficiency for a multiple order "deep" blazed diffraction grating having a 2.12 μm grating depth.
Figure 7A:
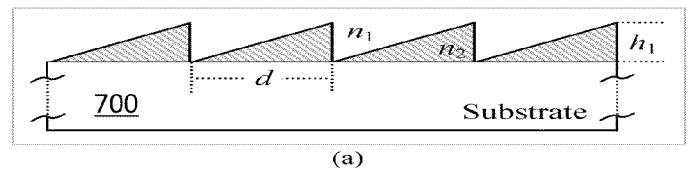
FIGS. 7A-7B illustrate single order and multiple order blazed gratings.
Figure 7B:
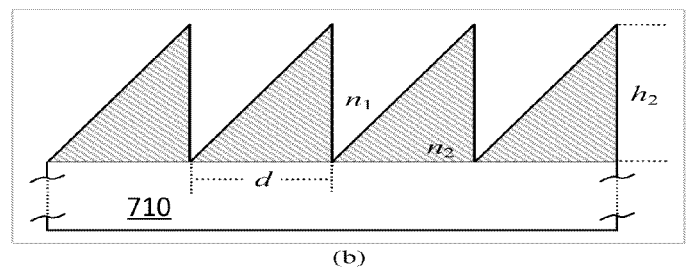

As shown above, in dual-band operation, an MWIR carrier frequency generated by a second order diffraction order is twice that of the LWIR carrier frequency generated by a first diffraction order. In additional examples, scene spatial information over a wide wavelength range can be modulated onto carrier frequencies that are spectrally dependent so that polarization information or spectral information can be extracted. In such applications, a 'deep', or multiple-order blazed grating (MBG) having multiple diffraction orders spanning the wavelength region of interest can be used. FIG. 6 is a graph of diffraction efficiency of such an MBG for a wavelength range spanning the visible and near infrared spectrum for diffraction orders 5-10. FIGS. 7A-7B are cross-sectional views of a single order BG 700 and an MBG 710. Both are defined by periodic steps of triangular cross-section between refractive indices $n_1$ and $n_2$ with period d, but the BG 700 has a height $h_1$ which is smaller than a height $h_2$ of the MBG 710.

Theoretical diffraction efficiency (DE) for an ideal blazed grating at a wavelength $\lambda$ in a diffraction order m can be calculated as $$DE(\lambda, m) = \text{sinc}^2\left(\frac{m - OPD}{\lambda}\right), \qquad (13)$$

wherein $$OPD = h(n_1 - n_2), \qquad (14)$$

and h is groove height, OPD is an optical path difference, and $n_i$, $n_2$ are indices of refraction for incident medium and blaze medium, respectively.

Example 6

Back-to-Back Grating Multispectral Snapshot Imaging Spectrometer

Figure 8A:
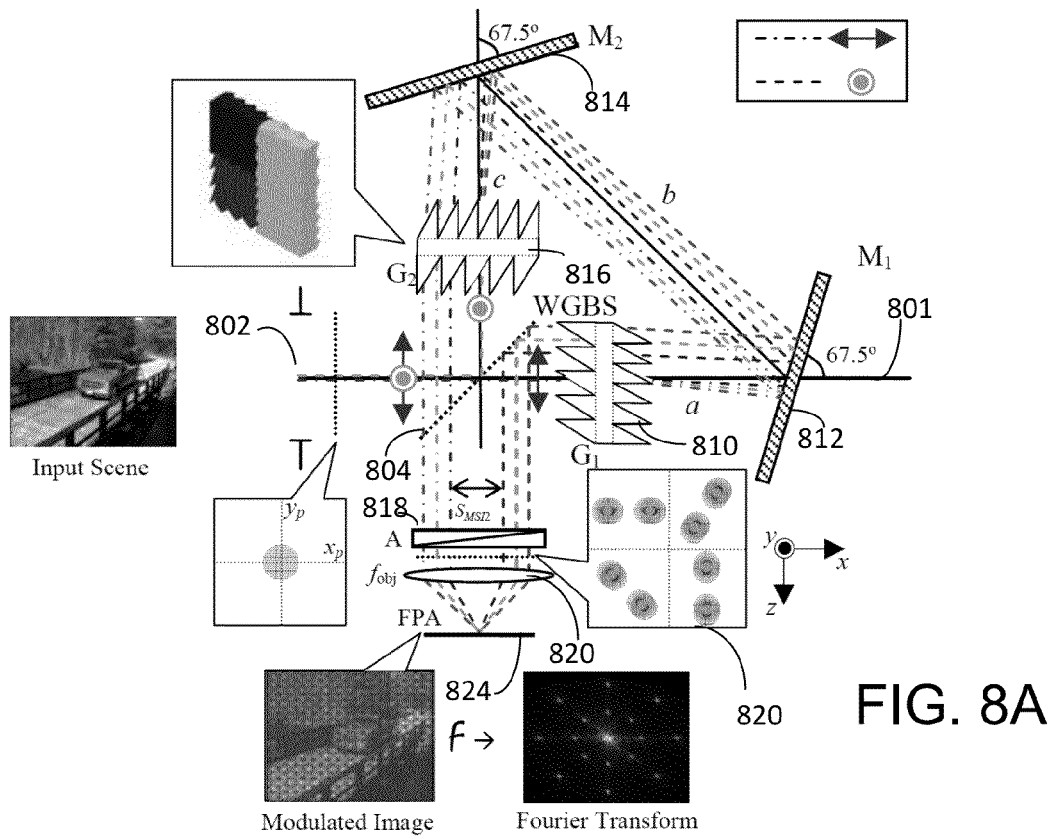
FIG. 8A illustrates a Sagnac interferometer based imaging polarimeter that includes multiple-order blazed gratings (MBGs) situated to provide multiple diffraction orders in two directions.

In other examples, multispectral polarimeters can include back-to-back gratings or grating assemblies with grating segments of various periods and orientation. With reference to FIG. 8A, a multispectral imaging polarimeter 800 includes an aperture 802 and a PBS 804 situated along an axis 801 and configured to receive an input optical flux, typically an optical flux associated with a two dimensional scene. The PBS 804 is situated to transmit a first polarization component of the input output flux to a first multi-wavelength blazed grating (MBG) 810, mirrors 812, 814, a second MBG 816 for transmission by the PBS 804 to a linear polarizer 818. An objective lens 820 focuses the received flux onto a focal plane array detector (FPA) 824. The PBS 804 is situated to reflect a second polarization component of the input output flux to the second MBG 816, mirrors 814, 812, the first MBG 810 for reflection by the PBS 804 to the linear polarizer 818. The objective lens 820 focuses the received flux onto the FPA 824 in combination with the flux transmitted by the PBS 804. As a result, a fringe pattern is formed on the FPA 824, with spatial carrier frequencies proportional to diffraction order.

Figure 8B:
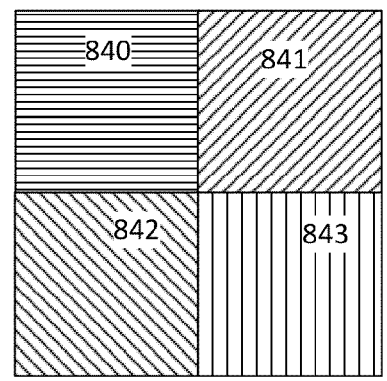
FIG. 8B illustrates a grating assembly that provides multiple diffraction orders in a plurality of directions.

The MBGs 810, 812 can be deep gratings as described above and shown in FIG. 7B. Such gratings produce fringe modulations at a variety of frequencies for corresponding spectral components of the scene optical flux based. Back to back gratings or multi-segmented gratings can be used. In the example of FIG. 8A, the MBGs 810, 812 are multi-segmented gratings as shown in FIG. 8B. For example, the MBG 810 can comprise grating segments 840-843 each having a different orientation and grating period. The grating segments can be low order blazed gratings or MBGs as well. The grating segments 840-843 can produce shears of different magnitudes and in different directions. In one example, an intensity distribution 820 is illustrated in a plane perpendicular to a z-axis (direction of optical flux propagation) and situated between the lens 820 and the analyzer 818. Shear of the input optical flux to locations displaced along both the x-axis and the y-axis and combinations of such shears is apparent.

If a linear polarizer is inserted with its axis at 45° with respect to the x-axis, then the Stokes vector incident on the PBS 804 is given by:

$$S_{WGBS} = \frac{1}{2}\begin{bmatrix} 1 & 0 & 1 & 0 \\ 0 & 0 & 0 & 0 \\ 1 & 0 & 1 & 0 \\ 0 & 0 & 0 & 0 \end{bmatrix}\begin{bmatrix} S_{0,inc} \\ S_{1,inc} \\ S_{2,inc} \\ S_{3,inc} \end{bmatrix} = \begin{bmatrix} S_{0,inc} + S_{2,inc} \\ 0 \\ S_{0,inc} + S_{2,inc} \\ 0 \end{bmatrix}. \quad (15)$$

$S_{0,inc}$, $S_{1,inc}$, $S_{2,inc}$, and $S_{3,inc}$ are the incident Stokes parameters at the linear polarizer and are implicitly dependent upon wavelength ($\lambda$). Substituting the values from $S_{WGBS}$ for the Stokes parameters from the equations above yields:

$$S'_0(m) = S'_2(m) = \int_{\lambda_{min}}^{\lambda_{max}} DE^2(\lambda, m)[S_{0,inc}(\lambda) + S_{2,inc}(\lambda)]d\lambda, \quad (16)$$

Substituting the values for $S_0'(m)$, $S_2'(m)$, and $S_3'(M)$ yields the intensity pattern:

$$I_{MSI}(x_i, y_i) = \quad (17)$$
$$\frac{1}{2}\sum_{m=0}^{Ce[\lambda_1/\lambda_{min}]}[S''_0(m)] + \frac{1}{2}\sum_{m=1}^{Ce[\lambda_1/\lambda_{min}]}\left[S''_0(m)\cos\left(\frac{2\pi}{f_{obj}}\frac{2m}{d}(a+b+c)x_i\right)\right],$$

wherein $$S''_0(m) = \int_{\lambda_{min}}^{\lambda_{max}} DE^2(\lambda, m)[S_{0,inc}(\lambda) + S_{2,inc}(\lambda)]d\lambda. \quad (18)$$

It should be noted that the dominant orders experimentally observed in the system correspond to the ceiling (Ce) of $\lambda_1/\lambda_{min}$, where $\lambda_1$ is the first order blaze wavelength of the diffraction grating. This changes the maximum limit of the summation from $d/\lambda_{min}$ to $Ce[\lambda_1/\lambda_{min}]$.

Example 7

Combined Gratings/Reflectors

Figure 9:
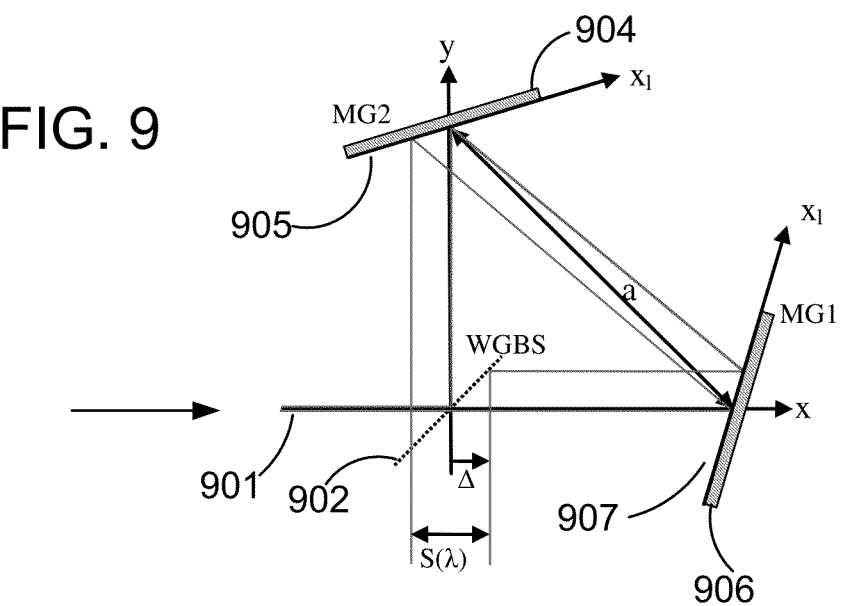
FIG. 9 illustrates a Sagnac interferometer system that includes diffraction gratings formed on mirror surfaces.

With reference to FIG. 9, a Sagnac interferometer based polarimeter includes a wire grid beam splitter (WGBS) 902 and mirrors 904, 906 that include diffraction gratings 905, 907 at respective mirror surfaces. Shear is dependent on pupil position in the y-plane due to the variation in separation along the mirror local x-axes $x_l$. The on-axis shear is:

$$S(\lambda) = \frac{2am\lambda}{d} \quad (19)$$

wherein a is a separation between mirrors 904, 906 along an optical axis 901 and is a function of $x_l$. To correct or compensate, a slowly varying chirp can be added to the blazed gratings on the mirrors 904, 906 such that a grating period d depends upon $x_l$. With such a modification, shear S can be constant or nearly so over the entire pupil.

Example 8

Serial or Parallel Sagnac Interferometer Systems

Figure 11A:
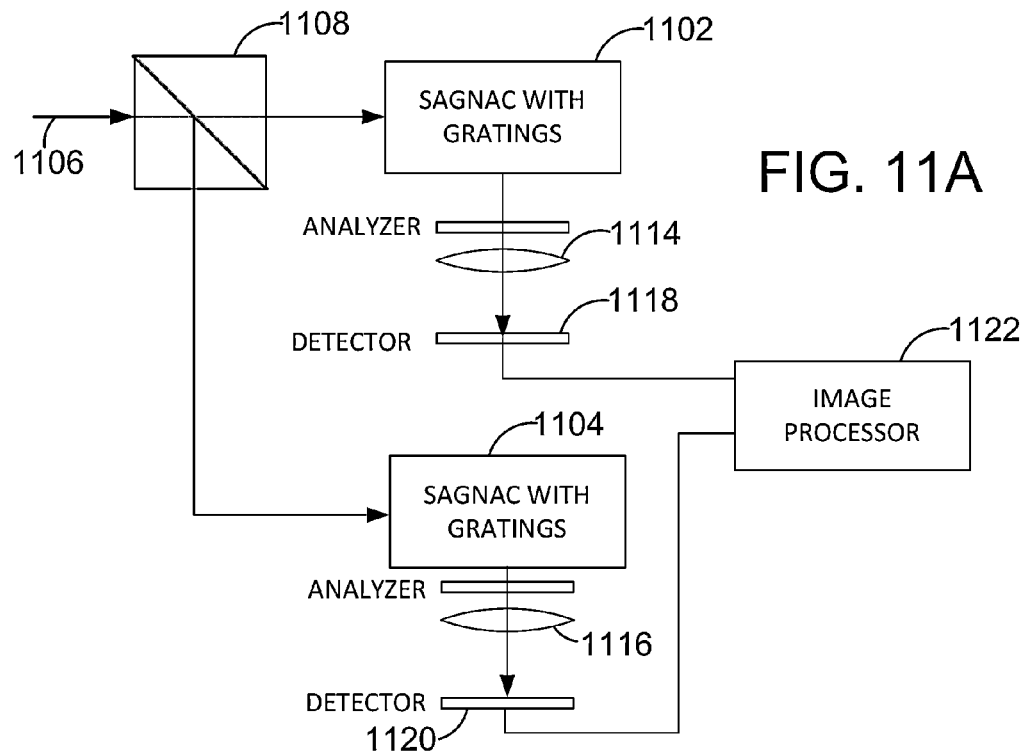
FIGS. 11A-11B illustrate polarimeters based on parallel or serial arrangements of Sagnac interferometers.
Figure 11B:
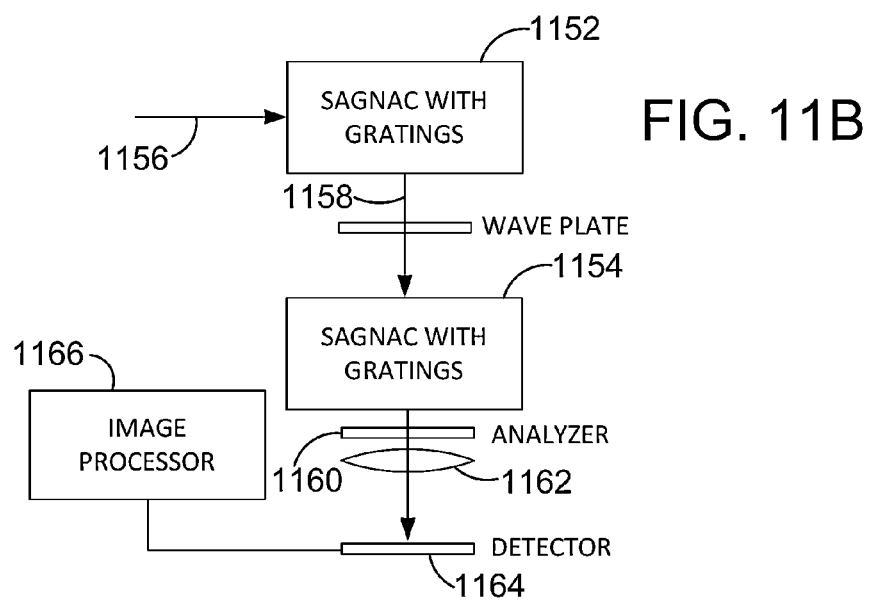

In some applications, determination of all four Stokes parameter may be desirable. Representative systems are illustrated in FIGS. 11A-11B. Referring to FIG. 11A, first and second Sagnac interferometer systems 1102, 1104 that include diffraction gratings as described in the examples above are configured to receive respective portions of an input optical flux 1106 from a beam splitter 1108. Typically, the beam splitter 1108 is substantially polarization independent, and can be provided as a plate beam splitter or other suitable optical element. The Sagnac interferometers direct sheared optical fluxes to respective polarizers (or other polarization components) 1110, 1112, lenses 1114, 1116, and array detectors 1118, 1120, respectively. An image processor 1122 receives detected interference signals from the array detectors 1118, 1120, respectively, and produces estimates of some or all Stokes parameters.

FIG. 11B illustrates a representative serial configuration that permits estimation of all four Stokes parameters. This configuration includes Sagnac interferometer systems 1152, 1154 situated in series. The interferometer 1152 is situated to receive an input optical flux 1156 and produce a sheared output flux 1158 that is directed to a retarder such as a quarter waver retarder or half wave retarder or other retarder and directed to the interferometer 1154. The interferometer 1154 provides additional shear and the sheared output is directed to an analyzer 1160, a lens 1162, and an array detector 1164. A detected interference pattern is evaluated in an image processor 1166 that is configured to identify one or more spatial frequency components in the detected interference pattern so as to provide estimates of one or more Stokes parameters.

The interferometers 1152, 1154 can be configured so as to produce interference patterns at different spatial frequencies based on, for example, diffraction grating periods, diffraction orders, or grating or mirror spacings. Modulations imposed by the interferometers can be detected based on these differing spatial frequencies. Alternatively, the interferometers 1152, 1154 can be configured to provide modulations at spatial frequencies associated with different spatial directions. For example, a first interferometer can provide an x-modulation and a second interferometer can provide a y-modulation that can be at the same or different spatial frequency so that modulation associated with the Stokes parameters can be identified based on either direction or spatial frequency or both.

Additional Examples

The examples above are representative only and are selected for purposes of illustration. In other examples, the same or different combinations of polarization parameters such as Stokes parameters can be estimated, and interferometers that include additional reflective surfaces and/or diffraction gratings can be used. Some examples are described with respect to linear polarizers, but in other examples, circular polarizers can be used. In view of the many possible embodiments to which the principles of the disclosed technology may be applied, it should be recognized that the illustrated embodiments are only preferred examples and should not be taken as limiting. I claim as my invention all that comes within the scope and spirit of the appended claims.

I claim:

1. An apparatus, comprising:
   a Sagnac interferometer that includes a pair of diffraction gratings so as to produce a dispersion compensated shear between first and second portions of an input light flux, the Sagnac interferometer comprising a polarizing beam splitter that directs the first and second portions of the input light flux along respective interferometer optical paths to the pair of diffraction gratings;
   a polarization analyzer situated to receive a combination of the sheared first and second portions of the input light flux and produce an associated output light flux;
   a detector situated to receive the output light flux and produce an image signal; and
   an image processor that produces a polarization image based on the image signal.

2. The apparatus of claim 1, wherein the Sagnac interferometer includes:
   at least two mirrors situated so that the first portion and the second portion of the input light are reflected and transmitted, respectively, by the polarizing beam splitter, the at least two mirrors and the polarizing beam splitter defining the Sagnac interferometer optical paths.

3. The apparatus of claim 2, wherein the at least two mirrors comprise a first mirror and a second mirror, and the pair of diffraction gratings comprises a first diffraction grating and a second diffraction grating, the first diffraction grating and the second diffraction grating situated along the Sagnac interferometer optical paths between the first mirror and the polarizing beam splitter and the second mirror and the polarizing beam splitter, respectively.

4. The apparatus of claim 3, wherein the first and second gratings are configured so that diffraction of the first and second portions of the input optical flux by both of the first and second gratings directs the first and second portions so as to be directed along the Sagnac interferometer optical paths so as to propagate displaced from and parallel to the Sagnac interferometer optical axis at the polarizing beam splitter.

5. The apparatus of claim 4, wherein the first and second gratings are situated a distance b from the first mirror and the second mirror respectively, and the first mirror and the second mirror are separated by a distance a along the Sagnac interferometer optical paths such that the dispersion compensated shear is proportional to $\lambda(a+2b)$, wherein $\lambda$ is a wavelength associated with the input optical flux.

6. The apparatus of claim 4, wherein the first and second gratings have a common grating period and are situated with respect to the Sagnac interferometer axis so as diffract into a common diffraction order and produce dispersion compensated shear that is proportional to a grating diffraction order n.

7. The apparatus of claim 1, wherein the image processor selects at least one spatial frequency component of the recorded image signal and determines an image polarization characteristic based an intensity modulation associated with an image signal variation at the selected spatial frequency.

8. The apparatus of claim 1, wherein shear for a spectral component of the input optical flux is proportional to a wavelength associated with the spectral component.

9. The apparatus of claim 1, wherein the polarization image is a two dimensional image.

10. The apparatus of claim 1, wherein the dispersion compensated shear is associated with spatial frequency components for a plurality of input optical flux spectral components, and the image processor estimates at least one polarization characteristic associated with the spatial frequency components based on image signal modulation at the corresponding spatial frequency.

11. The apparatus of claim 1, wherein the Sagnac interferometer produces the dispersion compensated shear between first and second portions based on counter-propagation of the first and second portions of the input light flux.

12. A method, comprising:
    receiving an input optical flux;
    directing first and second portions of the input optical flux along optical paths in a Sagnac interferometer with a polarizing beam splitter;
    diffracting each of the first and second portions of the input optical flux at at least one diffraction grating so as to produce a shear having a magnitude associated with a grating period and diffraction order and that is proportional to a wavelength of the input optical flux; and
    estimating a polarization characteristic of the input optical flux based on a spatial frequency associated with the shear in an intensity pattern obtained by directing the sheared first and second portions to a polarization analyzer and combining the sheared, polarization analyzed first and second portions of the input optical flux.

13. The method of claim 12, wherein the shear is produced so as to be inversely proportional to a grating period and directly proportional to a grating order.

14. The method of claim 12, wherein the first and second portions are combined with at least one focusing optical element of focal length f, wherein the spatial frequency is inversely proportional to f.

15. The method of claim 12, wherein the first and second portions of the input optical flux are directed so as to counter-propagate in the Sagnac interferometer along a common path.

16. The method of claim 12, wherein the first and second portions of the input optical flux are directed so as to counter-propagate in the Sagnac interferometer.

17. The method of claim 12, further comprising selecting spatial frequencies for at least two optical spectral components, and directing the first and second portions of the input optical flux to at least two diffraction gratings that are situated to diffract the at least two optical spectral components into different diffraction orders.

18. The method of claim 12, wherein the Sagnac interferometer includes a polarizing beam splitter and a first diffraction grating and a second diffraction grating situated to receive components of the input optical flux from the polarizing beam splitter such that the first and second diffraction gratings direct the received components to respective reflective surfaces such that the spatial frequency is a function of the separations between the diffraction gratings and the associated reflective surfaces, and a separation of the mirror surfaces.

19. A polarimeter, comprising:
    a Sagnac interferometer defined by a polarizing beam splitter, first and second diffraction gratings and associated first and second reflectors, such that first and second polarization components of an optical flux directed to the polarization beam splitter counter-propagate from the polarizing beam splitter, the first polarization component propagating to the first grating, the first reflective surface, the second reflective surface, the second grating, and the polarization beam splitter, and the second polarization component propagating to the second grating, the second mirror, the first grating and to the polarization beam splitter, wherein the Sagnac interferometer produces a shear between first and second counter-propagating polarization components that is a function of at least one of diffraction grating period, diffraction order, separation of diffraction gratings and respective reflective surfaces, and separation of the first and second reflective surfaces;

a focusing element that combines the counter-propagating portions of the input optical flux to produce an intensity pattern;

a polarization analyzer situated to receive the combined counter-propagating portions of the input optical flux so that the intensity pattern is based on the combined, polarization analyzed, counter-propagating portions of the input optical flux;

a detector that receives the intensity pattern and produce a detected intensity pattern; and an image processor that produces a polarization image based on the detected intensity pattern.

* * * * *